United States Patent [19]

Charles et al.

[11] Patent Number: 5,489,653
[45] Date of Patent: Feb. 6, 1996

[54] WATER-SOLUBLE COMPOUNDS DERIVED FROM HOMOPOLYMER OR COPOLYMER OF MALEIC ANHYDRIDE, AND APPLICATIONS OF THE SAID COMPOUNDS TO SUPPORTING BIOLOGICAL MOLECULES

[75] Inventors: Marie-Helene Charles, Condrieu; Thierry Delair, Lyon; Monique Jaubert, Craponne; Bernard F. Mandrand, Villeurbanne, all of France

[73] Assignee: Bio Merieux, Marcy l'Etoile, France

[21] Appl. No.: 32,027

[22] Filed: Mar. 16, 1993

[30] Foreign Application Priority Data

Mar. 17, 1992 [FR] France .................... 92 03425

[51] Int. Cl.$^6$ .................................................. C08F 8/34
[52] U.S. Cl. ........................ 525/327.5; 525/327.6; 525/350; 525/379; 525/380; 525/381; 525/382
[58] Field of Search .................... 525/327.6, 327.5, 525/350, 379, 380, 381, 382

[56] References Cited

U.S. PATENT DOCUMENTS

| | | | |
|---|---|---|---|
| 3,203,935 | 8/1965 | Miranda et al. | 525/380 |
| 3,310,540 | 3/1967 | Fang . | |
| 3,497,550 | 2/1970 | Samour | 526/312 |
| 4,013,511 | 3/1977 | Goldstein et al. . | |
| 4,182,752 | 1/1980 | Maeda et al. . | |
| 4,308,188 | 12/1981 | Wicks et al. | 525/327.6 |

FOREIGN PATENT DOCUMENTS

| | | |
|---|---|---|
| 0273895 | 7/1988 | European Pat. Off. . |
| 1580038 | 8/1969 | France . |
| 2384811 | 10/1978 | France . |
| 1745954 | 9/1971 | Germany . |
| 2420747 | 11/1974 | Germany . |

OTHER PUBLICATIONS

B. Solomon et al., "Studies on Adsorption of Amyloglucosidase on Ion-Exchange Resins", *Biotechnology and Bioengineering*, vol. XVI, pp. 1161–1177 (1974).

L. Goldstein et al., "Water-Insoluble Derivatives of Naringinase", *Int. F. Biochem.*, pp. 448–456, 1971.

*Primary Examiner*—Bernard Lipman
*Attorney, Agent, or Firm*—Oliff & Berridge

[57] ABSTRACT

Water-soluble compound derived from a homopolymer or copolymer of maleic anhydride having available anhydride functional groups and hydrolyzed anhydride functional groups, wherein the hydrolyzed anhydride functional groups consist of carboxyl functional groups and functional groups derived from carboxyl functional groups carrying a residue of a compound corresponding to the formula I:

$$C_xH_yA_zO_t$$

in which:

A is the nitrogen atom of a primary, secondary or tertiary amine functional group or the sulfur atom of a thiol functional group, x, z and t, independently of each other, are non-zero integers, and y is a non-zero integer, not less than 5 when A is a nitrogen atom and not less than 4 when A is a sulfur atom.

8 Claims, 1 Drawing Sheet

WATER-SOLUBLE COMPOUNDS DERIVED FROM HOMOPOLYMER OR COPOLYMER OF MALEIC ANHYDRIDE, AND APPLICATIONS OF THE SAID COMPOUNDS TO SUPPORTING BIOLOGICAL MOLECULES

The present invention relates to a water-soluble compound of a homopolymer or copolymer of maleic anhydride, to an agent for the hydrophilization of such a homopolymer or copolymer, to a process for preparing said water-soluble compound and finally to the applications of the compound prepared.

BACKGROUND OF THE INVENTION

The homopolymers of maleic anhydride or copolymers based on non-hydrolyzed maleic anhydride are insoluble in water at neutral pH. They become gradually soluble by hydrolysis reaction in aqueous medium, due to opening of the maleic anhydride rings by nucleophilic attack of the water molecules on the anhydride functional groups and subsequent opening of the rings with production of carboxyl functional groups.

Direct solubilization in aqueous medium by hydrolysis of the anhydride functional groups has the disadvantage of being a process which is lengthy and difficult to control. Indeed, it is not known how many anhydride functional groups are consumed in order to "dissolve" the polymer.

Moreover, it is known that the homopolymers or copolymers of maleic anhydride are soluble in certain organic solvents.

DESCRIPTION OF THE PRIOR ART

B. Solomon and Y. Levin (Biotechnology and Bioengineering, vol. XVI, pages 1161–1177 (1974)) have described a process for coupling an enzyme to ethylene-maleic anhydride copolymers, according to which the maleic anhydride copolymer, dissolved in acetone at a concentration of 10% (weight/volume), is mixed with an enzymatic preparation in order to fasten the latter to the copolymer. By a competitive effect between the water molecules of the enzymatic preparation and the amino groups of the enzyme, hydrolysis of the copolymer is produced which makes possible both its dissolution and fastening of the protein fraction. However, as explained in this publication, a partial precipitate of the ethylene-maleic anhydride copolymer is formed during mixing of the organic solution containing the copolymer and the protein solution, which necessitates an additional stirring stage lasting at least one night, until complete dissolution of the precipitate is obtained. This process is thus not entirely satisfactory because it exhibits technical implementational difficulties due to the formation of this precipitate.

One solution to overcome this problem could be found in the publication by Léon Goldstein et al. (Int. J. Biochem. 2, 448, 1971, Water-insoluble derivatives of naringinase) which consists in mixing the maleic anhydride copolymer in a solution containing approximately 50 to 70% of an organic solvent such as acetone, dimethylformamide (DMF) or dimethyl sulfoxide (DMSO) for complete dissolution of the copolymer and in adding the maleic anhydride copolymer solution thus obtained to an aqueous solution of an enzyme in order to fasten the latter to the copolymer. A homogeneous phase is effectively obtained.

However, this solution is particularly disadvantageous when the enzyme or any other biological molecule to be fastened to the homopolymer or copolymer is sensitive to the organic solvent, risking being partially, or indeed entirely, denatured and, for this reason, losing all biological activity.

According to DE 2,420,747, there is described a water-soluble compound derived from a maleic anhydride-ethylene copolymer intended to immobilize enzymes.

This derivative has hydrolyzed anhydride functional groups which consist of carboxyl functional groups carrying a residue of an amine chosen from hydrazine, p,p'-diaminodiphenylmethane (MDA) and 1,6-diaminohexane. The fastening of one or the other of these amines to the said copolymer confers on it a certain solubility in the aqueous phase thus making it possible to carry out the stage of fastening of the enzyme to the said derivative in aqueous medium. However, before the fastening stage, an additional stage of activation of the converted anhydride groups is required.

SUMMARY OF THE INVENTION

The present invention makes it possible to solve the problems posed by the currently existing solutions by providing a water-soluble compound derived from a homopolymer or copolymer of maleic anhydride which can be used directly for immobilizing a biological molecule, without a prior activation stage being required.

According to the invention, this compound has available anhydride functional groups and hydrolyzed anhydride functional groups, the hydrolyzed anhydride functional groups consisting of carboxyl functional groups and of functional groups derived from carboxyl functional groups carrying a residue of a compound corresponding to the formula I:

$$C_x H_y A_z O_t$$

in which:

A is the nitrogen atom of a primary, secondary or tertiary amine functional group or the sulfur atom of a thiol functional group, x, z ant t, independently of each other, are non-zero integers, and y is a non-zero integer, not less than 5 when A is a nitrogen atom and not less than 4 when A is a sulfur atom.

Functional groups derived front carboxyl functional groups are especially selected from ester, amide and thiocarboxyl functional groups.

When A is the nitrogen atom, the compound I is advantageously chosen from tris(hydroxymethyl)aminomethane, 2-(2-aminoethylamino) ethanol, 2-amino-2-methyl-1,3-propanediol, diethanolamine, the polypeptides and preferably a polytyrosine or polyglycine, N-BOC-1,6-diaminohexane and the compounds corresponding to the general formulae, respectively:

(II) $HO-(CH_2)_n-NH_2$ (III) $HO-(CH_2-CH_2)_n-O-(CH_2-CH_2)_n-NH_2$ (IV) $HO-(CH_2-CH_2-O)_n-CH_2-CH_2-NH_2$ in which n is an integer between 1 and 50.

Preferably, n is between 1 and 10 and the compound II is chosen from ethanolamine and 2-(2-aminoethoxy)ethanol.

When A is the sulfur atom, the compound I is advantageously mercaptoethanol.

The water-soluble compounds of the invention derived from the copolymers of maleic anhydride are chosen from poly(maleic anhydride-ethylene), poly(maleic anhydride-styrene), poly(maleic anhydride-propylene) or poly(maleic anhydride-methyl vinyl ether).

Preferably, the copolymers comprise at least 5% of maleic anhydride units.

The water-soluble compound is used according to the invention for immobilizing at least one biological molecule, to which it is bonded directly or indirectly. The said biological molecule is especially chosen from proteins such as antibodies or fragments of antibodies or antigens; polypeptides; enzymes; small molecules such as haptenes; or fragments of nucleic acids.

The term "fragment of nucleic acid" as used in the present invention means a fragment of natural DNA or RNA or a natural or synthetic oligonucleotide or a fragment of synthetic DNA or RNA which is unmodified or which comprises one or a number of modified bases such as inosine, 5-methyldeoxycytidine, 5-(dimethylamino)deoxyuridine, deoxyuridine, 2,6-diaminopurine, 5-bromodeoxyuridine or any other modified base.

Thus, in order to immobilize proteins, the water-soluble compound of the invention is added to a protein solution, the amino groups of the proteins reacting with the anhydride functional groups still available, that is to say the non-hydrolyzed anhydride functional groups, to form covalent bonds with the compound derived from the homopolymer or copolymer.

DESCRIPTION OF THE PREFERRED EMBODIMENT

Figure 1:
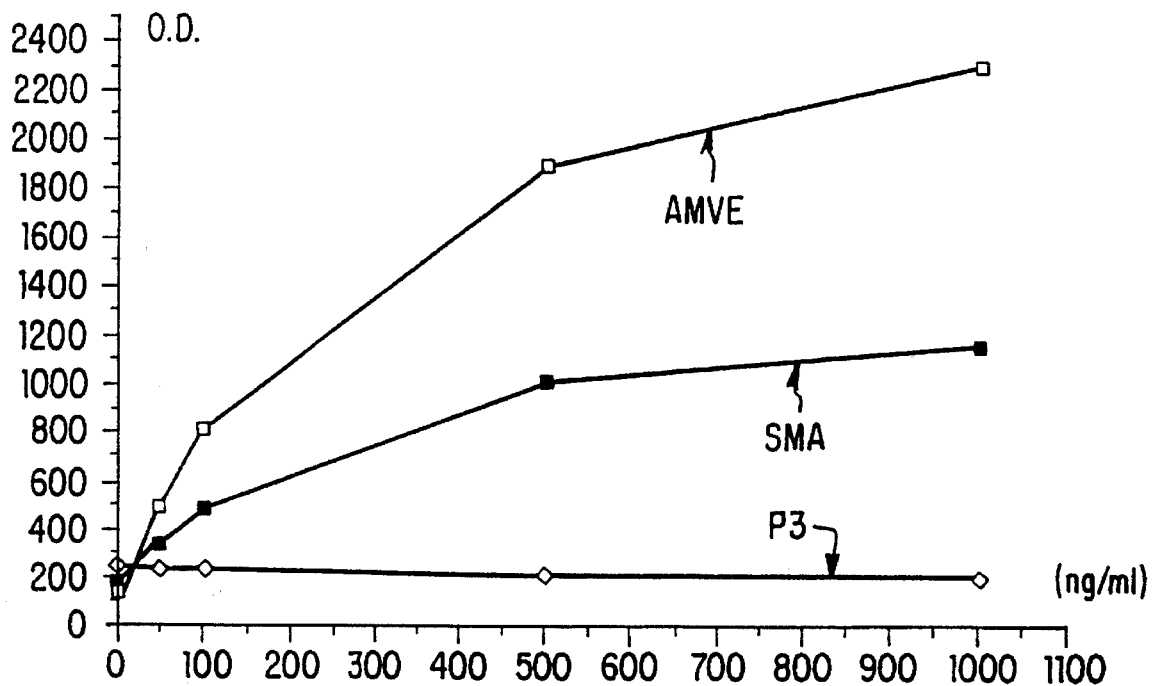
FIG. 1 shows the activity tests of immobilized antibodies, as seen in Example 6 below.

According to a particular embodiment of use of the compound of the invention, the latter is functionalized by interaction of the available anhydride functional groups with reactive functional groups of a functionalization agent, the said reactive functional groups being especially chosen from the amine, thiol and hydroxyl functional groups.

Within the meaning of the present invention, a functionalization is a chemical modification of the homopolymer or copolymer of maleic anhydride by a functionalization agent, for the purpose of:

1) its direct or indirect immobilization on a solid support: direct immobilization means the fastening by covalence or passive adsorption of the homopolymer or copolymer on the said solid support, which may or may not be functionalized beforehand; direct immobilization can be carried out by means of a ligand, fastened beforehand to the homopolymer or copolymer and then fastened chemically to the said solid support; indirect immobilization means the ligand/antiligand interaction between a ligand fastened to the homopolymer or copolymer and the antiligand or additional ligand fastened to the solid support 2) labeling it in order to detect it 3) the indirect fastening of a biological molecule to the said homopolymer or copolymer.

The functionalization agent is especially chosen from the haptenes, coloring agents, luminescent agents, fluorescent agents or phosphorescent agents and natural or synthetic polymers, especially polypeptides, polysaccharides and proteins which are soluble in organic medium, and N-BOC-1,6-diaminohexane.

According to the invention, the result is that if the bond between the compound of the invention and the biological molecule(s) is indirect, the compound is bonded to a functionalization agent which can belong to the group of agents mentioned above, the functionalization agent being itself bonded to the biological molecule(s).

Additionally, the compound carrying the biological molecule(s), which is functionalized or unfunctionalized, can he bonded directly or indirectly to a solid support. The compound can be directly bonded to a solid support by a ligand chosen especially from the polypeptides and polytyrosine and polyglycine and N-BOC-1,6-diaminohexane. When the bond between the compound and the solid support is indirect, the compound is bonded to a functionalization agent which is bonded to an additional functionalization agent, the latter being bonded to a solid support.

According to the invention, the compound corresponding to the formula I can be both the hydrophilization agent and the functionalization agent and is preferably a polypeptide chosen from polytyrosine and polyglycine or N-BOC-1,6-diaminohexane.

Advantageously, the solid support is chosen from chemically modified or nonmodified synthetic or natural materials and especially from latexes, polymers of the poly(vinyl chloride), polyethylene, polystyrene or polyacrylate type and copolymers of the styrene-based type.

The solid support can be in the form of a microtitration plate, a cone, a tube, a well, balls or similar.

The present invention also relates to an agent for the hydrophilization of a homopolymer or copolymer of maleic anhydride, this agent corresponding to the formula I:

in which:

A is the nitrogen atom of a primary, secondary or tertiary amine functional group or the sulfur atom of a thiol functional group, x, z and t, independently of each other, are non-zero integers, and y is a non-zero integer, not less than 5 when A is a nitrogen atom and not less than 4 when A is a sulfur atom.

The hydrophilizing agent is a compound which is soluble both in water and in organic medium and capable of fastening to the homopolymer or copolymer of maleic anhydride to make it entirely soluble in a largely aqueous phase.

Another subject of the invention is a process for producing a derivative, soluble in the aqueous phase at neutral pH, of a homopolymer or copolymer of maleic anhydride, consisting:

in dissolving the homopolymer or copolymer in an anhydrous organic solvent and in reacting the homopolymer or copolymer in solution with the hydrophilizing agent of the invention, in the organic phase.

For the implementation of this process, and in particular for the dissolution stage, the solvent employed is preferably of polar aprotic type such as dimethylformamide (DMF), dimethyl sulfoxide (DMSO), pyridine, 1,3-dimethyl-3,4,5,6-tetrahydro-2(1H)-pyrimidinone, dioxane or similar.

The amount of solvent to use depends on the chemical nature of the homopolymer or copolymer, on its molecular weight and on the nature of the organic solvent. In addition, for two polymers of identical molecular weight, the more hydrophobic polymer will dissolve more easily in the organic solvent. The amount of solvent is at least equal to the amount necessary to dissolve the homopolymer or copolymer at room temperature, but can be greater without having any harmful effect on the progress of the process.

Finally, a final subject of the invention is a process for immobilizing a biological molecule on a homopolymer or copolymer of maleic anhydride, consisting:

in dissolving the homopolymer or copolymer in an anhydrous organic solvent and in reacting the dissolved homopolymer or copolymer with a hydrophilizing agent according to the invention, in the organic phase, and in bringing the water-soluble compound obtained into contact with the biological molecule, in the aqueous phase.

The immobilization process of the invention can additionally comprise, before bringing the water-soluble compound into contact with the biological molecule, a functionalization stage:

of the homopolymer or copolymer of maleic anhydride, when it is carried out before the hydrophilization stage of the said homopolymer or copolymer or of the water-soluble compound, when it is carried out after the hydrophilization stage of the homopolymer or copolymer.

The functionalization stage is carried out in the organic phase with a functionalization agent which is advantageously chosen from the haptenes, coloring agents, luminescent agents, fluorescent agents or phosphorescent agents and natural or synthetic polymers, especially polypeptides, polysaccharides and proteins soluble in the organic medium, and N-BOC-1,6-diaminohexane.

The functionalization reaction takes place at temperatures of between +4° C. and +50° C., preferentially between +4° C. and +37° C., and more commonly at room temperature. The contact time between the functionalization agent(s) and the homopolymer or copolymer ranges between 30 min and 48 hours, preferentially between one hour and 24 hours. Stirring of the reaction mixture is not always essential.

The various subjects of the invention, and their characteristics and advantages, are now illustrated by Examples 1 to 6 which follow:

EXAMPLE 1

Preparation of Water-soluble Compounds Derived from Maleic Anhydride Copolymers

Table 1 which follows displays the conditions for the preparation of a water-soluble compound derived from three maleic anhydride copolymers, respectively A, B and C:

Copolymer A marketed by the Company Polyscience under reference 3106

Copolymer B marketed by the Company Janssen under reference 17.923–77

Copolymer C marketed by the Company Polyscience under reference 3102.

According to the process of the invention, the copolymer is dissolved in an anhydrous organic solvent, anhydrous dimethylformamide (DMF), and then the hydrophilizing agent, ethanolamine, is added in organic medium. The amount of hydrophilizing agents in general and of ethanolamine in particular to use for this example depends on the chemical nature of the polymer or copolymer, on the concentration of the polymer or copolymer in the organic phase and on the volume of the aqueous phase. The amount of hydrophilizing agent added depends essentially on the intrinsic hydrophilicity of the polymer or copolymer.

Thus, Table 1 gives the amounts of ethanolamine necessary for 100 µl of solution of a water-soluble compound derived from copolymers A, B and C respectively, diluted in 900 µl of aqueous medium, to provide a homogeneous solution.

TABLE 1

| 50/50 Copolymer maleic anhydride/P | A | B | C |
|---|---|---|---|
| P | styrene | styrene | methyl vinyl ether |
| $M_w$ (molecular mass) | 1600 | 50,000 | 67,000 |
| Amount of copolymer (mg) | 100 | 50 | 15 |
| DMF (ml) | 1 | 1 | 1 |
| Ethanolamine (µl) | 15 | 7.5 | 1 |
| % of the anhydride functional groups consumed by the ethanolamine | 50 | 50 | 25 |

EXAMPLE 2

Immobilization of Allergens on a Water-soluble Compound Derived from the Maleic Anhydride-styrene Copolymer, B, of Example 1 and then Fastening to Particles of Functionalized Latex 7.5 µl of ethanolamine are added to 1 ml of a solution of B in anhydrous DMF and then the mixture is stirred for 30 sec. 4 µl of the solution of B diluted to 1/5 in DMF and 200 µl of aminated latex suspension having a 5% solids content (Société BioMérieux) are added successively to a 100 mM carbonate buffer, pH 8.2, containing 0.5 mg/ml of aqueous dactylis extract (Laboratoire des Stallergènes) in order to finally obtain a total volume of 1 ml. After gentle stirring for 18 hours, the latex is centrifuged for 5 min at 8000 rpm in a Eppendorf centrifuge. The pellet is taken up in a 0.1M glycine, 0.15M NaCl 5 g/l BSA buffer, pH 8.2.

\* Activity test of the immobilized allergens:

100 µl of latex suspension and 50 µl of serum are deposited in each well in a microtitration filtering plate (Company Pall). After incubating for 3 hours at room temperature, 2 washings by PBS-Tween are carried out by filtration under vacuum. 100 µl of anti-IgE antibodies labeled with horseradish peroxidase are then introduced and the mixture is left to incubate for 1 hour at room temperature before washing twice. 250 µl of ortho-phenylenediamine substrate are then added. After incubating for 30 min, the enzymatic reaction is blocked by addition of 100 µl of $H_2SO_4$, filtration is carried out in a microtitration plate and the optical density of the filtrate is read on a plate reader at a wavelength of 492 nm.

The results (expressed in O.D. units) are presented in the following Table 2:

TABLE 2

| | NEGATIVE SERUM | POSITIVE SERUM |
|---|---|---|
| Copolymer-free reference LATEX | 0.056 | 0.387 |

TABLE 2-continued

|  | NEGATIVE SERUM | POSITIVE SERUM |
| --- | --- | --- |
| Allergens immobilized on copolymer fastened to LATEX | 0.064 | 1.050 |

The system exhibits low background noise and the specific signal is high.

EXAMPLE 3

Immobilization of Allergens on a Compound Derived from the Maleic Anhydride-styrene Copolymer, B, of Example 1 and then Fastening of the Said Derivative to a Solid Support

* Functionalization by biotin and then hydrophilization of copolymer B 1 ml of a solution of B in anhydrous DMF is added to 1 mg of biotin hydrazide (Pierce) and the mixture is left to react for two hours at room temperature. The copolymer can be used as it is without any purification stage.

7.5 µl of ethanolamine as hydrophilizing agent are added to the solution of functionalized copolymer.

* Immobilization of allergens on the non-functionalized part of the derivative of copolymer B prepared above:

The copolymer thus obtained is then diluted by 1/10 in DMF and 2.5 µl of copolymer/biotin mixture are added to 0.5 ml of a solution of allergens, extracted from dactylis (Laboratoire des Stallergènes), containing 0.5 mg/ml of proteins. After incubating for 4 hours at room temperature, dialysis is carried out for 18 hours at +4° C. against a 20 mM phosphate buffer, pH 7.4.

* Fastening of the functionalized part of the derivative of copolymer B to a solid support carrying an anti-biotin antibody:

50 µl of the solution of allergens prepared above is deposited in a tube on which an anti-biotin antibody is adsorbed, and incubation is carried out for one hour at room temperature.

* Activity test of the immobilized allergens:

After two washings in PBS Tween, 50 µl of serum are added and incubation is carried out for 2 hours at room temperature. After 2 new washings, 100 µl of anti-IgE antibodies labeled with peroxidase are added and incubation is carried out for one hour at the same temperature. After washing, the enzymatic reaction takes place for 30 min at room temperature. After blocking with 1 ml of sulfuric acid, reading is carried out at 492 nm.

The results, expressed in optical density units, are the following:

NEGATIVE SERUM: 0.014
POSITIVE SERUM: 1.533

The system thus obtained exhibits a very low background noise and a good specific signal.

EXAMPLE 4

Immobilization of Allergens on a Maleic Anhydride-styrene Copolymer Functionalized and Hydrophilized by the Same Agent, Polytyrosine

* Functionalization of the copolymer:

10 mg of styrene-maleic anhydride copolymer with a molecular weight of 360,000 are dissolved in 1 ml of DMF. 1 ml of a 2 mg/ml solution of polytyrosine (Sigma, molecular weight 27,000) in DMSO is then added. The mixture is left to react for 3 hours at room temperature. The copolymer becomes sufficiently hydrophilic to be used as it is under the conditions developed for fastening allergens.

* Immobilization of the allergens:

5 µl of a solution of functionalized copolymer are added to 995 µl of a 0.5 mg/ml solution of allergens (Artemisia extract from Laboratoire des Stallergènes) in a 100 mM carbonate buffer, pH 8.2, and incubation is carried out for 4 hours at room temperature.

* Activity test of the immobilized allergens on the water-soluble compound derived from B fastened to cones:

The allergen thus prepared is tested on the VIDAS system (BioMérieux registered trademark) after fixing to the cones according to a procedure specified by the manufacturer.

The results, expressed in relative fluorescence units: RFU, are the following:

NEGATIVE SERUM: 116
POSITIVE SERUM: 988

EXAMPLE 5

Immobilization of Allergens on the Water-soluble Compound Derived from a Maleic Anhydride Copolymer Functionalized and Hydrophilized by the Same Agent, N-BOC-1,6,-diaminohexane

* Functionalization and hydrophilization of the copolymer:

10 mg of styrene-maleic anhydride copolymer with a molecular weight of 360,000, are dissolved in 0.7 ml of DMSO. 0.3 ml of a 3 mg/ml solution of N-BOC-1,6-diaminohexane hydrochloride (Fluka) in DMSO, containing 10 µl of triethylamine (Janssen) per ml of solvent, is then added. The mixture is left to react for 3 hours at room temperature. The polymer becomes sufficiently hydrophilic to be used as it is, or diluted by half in DMF, under the conditions developed for fastening allergens.

* Immobilization of the allergens:

12.5 µl of a solution of functionalized copolymer diluted by half in DMF are added to 2490 µl of a 0.5 mg/ml solution of allergens (Dactylis extract from Laboratoire des Stallergènes) in a 100 mM carbonate buffer, pH 8.2, and incubation is carried out for 4 hours at room temperature.

* Activity test of the immobilized allergens:

The allergen thus prepared is tested on the VIDAS system (BioMérieux) after fixing to the cones according to a procedure specified by the manufacturer.

The results, expressed in relative fluorescence units: RFU, are the following:

HIGHLY POSITIVE SERUM (>60): 13,827
POSITIVE SERUM (15): 3,191
SLIGHTLY POSITIVE SERUM (1.4): 1,568
VERY SLIGHTLY POSITIVE SERUM (0.44): 255
NEGATIVE SERUM: 133

These methods of immobilization of allergens on a solid phase according to Examples 4 and 5 exhibit a marked advantage with respect to that described in Example 3 in that, being direct, they do not require the use of an anti-biotin antibody. The procedure is easy to use.

EXAMPLE 6

Immobilization of Anti-Alpha-Foetoprotein (Anti-AFP) Monoclonal Antibodies on the Water-soluble Compound Derived from a Copolymer of Maleic Anhydride B or C of Example 1, Functionalized by Biotin, and then Fastening to a Solid Support Carrying an Anti-biotin Antibody

* Functionalization of the copolymer:

Copolymer B is functionalized by biotin and made water-soluble according to the prototype described in Example 3.

Copolymer C is functionalized and made water-soluble as follows:

0.1 ml of 2.5 mg/ml biotin hydrazide solution is added to 1 ml of solution C. The mixture is left to react for two hours, after which the functionalized copolymer is treated with ethanolamine.

* Immobilization of the antibodies on the non-functionalized part of the derivative of copolymer B or C prepared above:

5 µl of a solution of functionalized water-soluble compound derived from copolymer B or C are added to a final 0.5 mg/ml solution of antibodies in a 100 mM carbonate buffer, pH 8.2. Incubation is carried out for 1 hour at 37° C. before dialyzing for 4 hours at room temperature against PBS.

* Fastening of the functionalized part of the compound derived from copolymer B or C to a solid support carrying an anti-biotin antibody:

An anti-biotin antibody, at a charge of 2 µg of antibody per well, is fixed to a microtitration plate (NUNC, commercial name) for 2 hours at 37° C. before saturation in 0.5% gelatin. A volume of immobilized anti-AFP antibody solution is deposited in the wells of the plate thus obtained. The plate is left for 1 hour at 37° C.

* Activity test of the immobilized antibodies:

After 3 washings in PBS Tween, an antigen (AFP) range is introduced. After leaving to incubate for 1 hour at 37° C., washing is carried out 3 times in PBS Tween. The presence of the antigen is detected by an additional alkaline phosphatase/polyclonal antibody conjugate. Incubation is carried out for 1 hour at 37° C. Visualization is carried out with the substrate paranitrophenyl phosphate (pNPP). After blocking with 1N NaOH, reading is carried out with a plate reader, at a wavelength of 405 nm.

The results obtained are shown in FIG. 1. The curve entitled P3 is that of the antibody alone. It is thus seen that the latter is not non-specifically adsorbed, or is only so adsorbed to a small degree, by the microtitration plate coated with anti-biotin antibody.

The curve entitled MVEMA is that obtained with methyl vinyl ether-maleic anhydride copolymer C. The curve denoted SMA is that obtained by using styrene-maleic anhydride copolymer B. The methyl vinyl ether-maleic anhydride copolymer gives stronger signals (curve MVEMA) than the styrene-maleic anhydride copolymer (curve SMA), everything else being otherwise equal (concentration of antibody during coupling, concentration of biotin on the polymer).

The methyl vinyl ether-maleic anhydride copolymer, which is more hydrophilic than the styrene-maleic anhydride copolymer, preserves the integrity of the antibody better while causing only a slight denaturing.

EXAMPLE 7

Use of a Water-soluble Compound Derived from Maleic Anhydride-methyl Vinyl Ether Copolymer, Functionalized by Biotin, as Chemical Amplifier In various biological phenomena, and very particularly in the field of diagnostics, in order to achieve high sensitivity levels, it may be necessary to artificially amplify a specific signal (for example: detection of biological material present in small amounts, such at DNAs or DNA fragments).

For this purpose, increasing amounts of biotin hydrazide (Pierce) were reacted with the maleic anhydride-methyl vinyl ether copolymer, C, of Example 2 to obtain functionalized copolymers. The latter were treated with ethanolamine in order to lead to water-soluble functionalized compounds which are called poly-biotin.

A constant amount of various poly-biotins is fixed, via an anti-biotin antibody immobilized at the bottom of the wells according to the method described in Example 5, in wells of a microtitration plate (NUNC). The presence of biotin is visualized by a streptavidin/peroxidase conjugate which is fixed by forming a complex with biotin.

Detection, using labeled streptavidin, diluted 1/10,000 in PBS/0.5% gelatin, is carried out in the following way:

incubation of the streptavidin/peroxidase conjugate for one hour at 37° C.;

3 washings in PBS Tween;

addition of the orthophenylenediamine (OPD) substrate, blocking with $H_2SO_4$ and reading at 492 nm.

Figure 2:
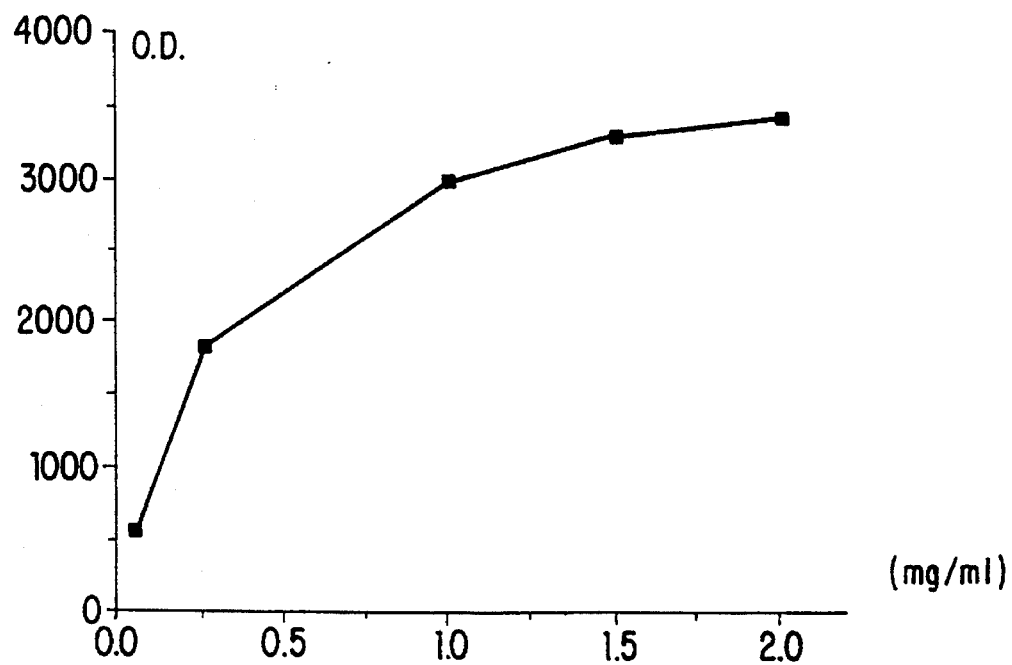
FIG. 2 shows the signal obtained as a function of the amounts of biotin fastened to the poly(methylvinylether-maleic anhydride), as seen in Example 7 below.

FIG. 2 shows the signal obtained as a function of the amounts of biotin fastened to the poly(methyl vinyl ether-maleic anhydride). It is observed that there is an amplification of the signal by a factor of approximately 6 when moving from 0.05 mg of biotin to 1.5 mg of biotin per 15 mg of polymer.

We claim:

1. A water-soluble compound derived from a homopolymer or copolymer of maleic anhydride, the compound having available anhydride functional groups sufficient to immobilize at least one biological molecule, and hydrolyzed anhydride functional groups, wherein the hydrolyzed anhydride functional groups consist of carboxyl functional groups and functional groups derived from carboxyl functional groups carrying a residue of a compound corresponding to the formula I:

$$C_xH_yA_zO_t$$

in which:

A is a nitrogen atom of a primary, secondary or tertiary amine functional group or a sulfur atom of a thiol functional group, x, z and t, independently of each other, are non-zero integers, and y is a non-zero integer, not less than 5 when A is a nitrogen atom and not less than 4 when A is a sulfur atom.

2. The compound as claimed in claim 1, wherein A is the nitrogen atom and the compound I is chosen from tris(hydroxymethyl)aminomethane, 2-(2-aminoethylamino)ethanol, 2-amino-2-methyl-1,3-propanediol, diethanolamine, the polypeptides and especially polytyrosine and polyglycine, N-BOC-1,6-diaminohexane and the compounds corresponding to the general formulae, respectively:

(II) $HO-(CH_2)_n-NH_2$ (III) $HO-(CH_2-CH_2)_n-O-(CH_2-CH_2)_n-NH_2$ (IV) $HO-(CH_2-CH_2-O)_n-CH_2-CH_2-NH_2$ in which n is an integer between 1 and 50.

3. The compound as claimed in claim 2, wherein n is between 1 and 10 and the compound II is chosen from ethanolamine and 2-(2-aminoethoxy)ethanol.

4. The compound as claimed in claim 1, wherein A is the sulfur atom and the compound I is mercaptoethanol.

5. The compound as claimed in claim 1, wherein the copolymers of maleic anhydride are chosen from poly(maleic anhydride-ethylene), poly(maleic anhydride-styrene), poly(maleic anhydride-propylene) or poly(maleic anhydride-methyl vinyl ether).

6. The compound as claimed in claim 5, wherein the copolymer of maleic anhydride comprises at least 5% of maleic anhydride units.

7. A process for producing the water-soluble compound of claim 1, comprising:

dissolving the homopolymer or copolymer in an anhydrous organic solvent; and reacting the homopolymer or copolymer with an agent capable of hydrophilizing the homopolymer or copolymer in organic phase.

8. The compound of claim 1, wherein said compound is prepared by partial amidization of said homopolymer or copolymer of maleic anhydride.

\* \* \* \* \*